United States Patent [19]

George

[11] Patent Number: 5,113,353
[45] Date of Patent: May 12, 1992

[54] RHEOMETRICS AND VISCOELASTICITY MEASUREMENT

[76] Inventor: Alan George, 238 Alwyn Road, Bilton, Rugby, Warwickshire, England

[21] Appl. No.: 253,544

[22] Filed: Oct. 5, 1988

[30] Foreign Application Priority Data

Oct. 9, 1987 [GB] United Kingdom ............... 8723796

[51] Int. Cl.$^5$ ............................................. G01N 11/08
[52] U.S. Cl. .................................. 364/508; 73/84.24
[58] Field of Search ............... 364/508, 509, 556, 557, 364/558; 73/766, 778, 781, 790, 807, 815, 54, 56, 59

[56] References Cited

U.S. PATENT DOCUMENTS

| | | | |
|---|---|---|---|
| 2,703,006 | 3/1955 | Savins | 74/54 |
| 3,128,620 | 4/1964 | Gupta | 74/56 |
| 3,494,172 | 2/1970 | Juve et al. | 74/54 |
| 3,710,614 | 1/1973 | Oppliger | 74/56 |
| 3,712,117 | 1/1973 | Fitzgerald et al. | 74/56 |
| 3,762,429 | 10/1973 | Fitzgerald et al. | 74/54 |
| 3,875,791 | 4/1975 | Fitzgerald et al. | 74/54 |
| 3,977,234 | 8/1976 | Lynch et al. | 73/54 |
| 4,241,602 | 12/1980 | Han et al. | 73/56 |
| 4,488,427 | 12/1984 | Matusik et al. | 74/54 |
| 4,524,610 | 6/1985 | Fitzgerald et al. | 74/54 |
| 4,566,181 | 1/1986 | Matusik et al. | 74/59 |
| 4,648,264 | 3/1987 | Freese et al. | 73/60 |
| 4,680,958 | 7/1987 | Ruelle et al. | 73/56 |
| 4,754,640 | 7/1988 | Fitzgerald et al. | 73/54 |
| 4,763,512 | 8/1988 | Taylor | 73/54 |

FOREIGN PATENT DOCUMENTS

| | | |
|---|---|---|
| 0007427 | 2/1980 | European Pat. Off. |
| 1298788 | 12/1972 | United Kingdom |
| 2123966 | 2/1984 | United Kingdom |
| 2142435 | 1/1985 | United Kingdom |
| 2173599 | 10/1986 | United Kingdom |

OTHER PUBLICATIONS

Sangamo Controls Limited; "Viscosity-Rheology"; 1962.
Sangamo Controls Limited; "Rheogoniometer"; Jun. 1966.
Sangamo Controls Limited; "Rheogoniometer"; Apr. 1964.
"A Process Analyser with a Versatile Microcomputer Control and Readout System", *Application of Microprocessors in Devices for Instrumentation and Automatic Control*, vol. 18, Nov. 1980, by A. George, pp. 221–231.

Primary Examiner—Parshotam S. Lall
Assistant Examiner—Ellis B. Ramirez
Attorney, Agent, or Firm—Young & Thompson

[57] ABSTRACT

A viscoelastic measurement device comprising a measurement chamber (10) to receive a sample whose viscoelasticity is to be measured, a displacement member (11) located in said chamber, displacement means (34) for displacing the displacement member within the measurement chamber and thereby applying a deformatory stress to a sample located therein, measurement transducer means (35) for detecting the input deformatory displacement, measurement transducer means (35) for detecting the output or reaction deformatory movement or action of the sample, calculator means (211) for calculating the viscoelasticity from the input and output data.

18 Claims, 10 Drawing Sheets

RHEOMETRICS AND VISCOELASTICITY MEASUREMENT

This invention relates to rheometric measurement, that is the behaviour and performance of solids under stress and is particularly, but not exclusively concerned with the measurement of viscoelasticity, or elasticity under applied stress, which is one of the key factors in determining rheological properties. Another factor is the melt flow index, the measurement of which is taught in our pending UK patent application no. 8723101.

Together, melt flow index and viscoelasticity may be said to define comprehensively the rheological properties of a material and are in practice all that is needed to identify performance characteristics and predict the behaviour of a material when it is 'worked' in manufacture, for example, extruded our moulded in the case of a synthetic plastics material from a melted and flowing ingredient.

In that regard, although the present invention is particularly concerned with viscoelasticity, the combined simultaneous measurement with melt flow index is possible by incorporating a supplementary measurement chamber in the same general controlled-environment mounting block, as discussed in our pending UK patent application no. 8723101.

Viscoelasticity is a factor of interest both to producers of bulk 'raw' plastics ingredient, for example granules, chips or powders, for subsequent manufacture, and the end-users themselves, who have to set their machines to suit the material input ingredient and the desired end-product. The structural and aesthetic characteristics can be impaired if the incorrect conditions are used.

Accordingly, the early recognition of material characteristic departures from the desired standard, and the prompt initiation of corrective control action—for example, revised machine settings—offers significant enhancements in the economics and quality of manufacture. This is particularly so if the cycle of (input) monitoring and (output) control is 'closed'—i.e. there is automatic feedback of corrective control action. Analogue techniques for achieving this typically require elaborate circuitry, with skilled and delicate setting up and adjustment in running. An MFI measurement technique that will be compatible with more 'robust' digital control is thus desirable.

There have been numerous previous proposals for tackling the problems of rheometric measurement. Also known is so-called 'rotational rheometry' in which a sample is subjected to torsional loading.

For example, UK patents nos. 2,123,966, 2,142,435, 2,173,599, and U.S. Pat. Nos. 3,128,620, 2,817,231 and 2,703,006, and EP 0,071,427 teach rheometers, but these are largely concerned with laboratory measurement under favourable environmental conditions.

According to one aspect of the invention there is provided a viscoelastic measurement device comprising:
a measurement chamber to receive a sample whose viscoelasticity is to be measured,
a displacement member located in said chamber,
displacement means for displacing the displacement member within the measurement chamber and thereby applying a deformatory stress to a sample located therein,
measurement chamber and thereby applying a deformatory stress to a sample located therein,
measurement transducer means for detecting the output or reaction deformatory movement or action of the sample,
calculator means for calculating the viscoelasticity from the input and output data.

According to another aspect of the invention there is provided a rheometric measurement device for affording data upon the rheological properties and thus the processability of a sample, in particular a polymer melt, including the measurement of elasticity under applied stress, in particular a rotational or torsional movement, that is by rotational rheology or rheometrics, and optionally the measurement of viscosity or melt flow index, the device comprising:
a sample chamber to receive a sample under test,
loading means for loading a sample into the chamber,
seal means for restraining the sample within the chamber,
pressurising means for pressurising the sample within the chamber or upon its entry thereinto,
pressure relief means for allowing the controlled egress of material from the chamber,
temperature control means for maintaining the sample at a predetermined temperature,
loading means for applying a cyclically repeated controlled loading force to the sample,
detector means for detecting the reaction of the sample to the applied loading,
computer means for computing from the reaction data the rheometric properties of the sample.

According to a further aspect of the invention there is provided a viscoelastometer for measuring the viscoelastic properties of a sample under varying applied stress and monitored strain reaction conditions and comprising:
a constant temperature enclosure,
means for loading or applying a constant temperature flow of sample material, or a polymer street, to the enclosure,
means for restraining the sample within the enclosure,
controlled exit means for allowing a controlled output of sample material from the enclosure,
a rotary loading member located within the enclosure and defining a marginal space therebetween and the enclosure walls,
controlled displacement means for cyclically moving the loading member within the enclosure,
sensor means for monitoring the displacement of the loading member and the reaction forces thereupon from the sample material within the enclosure to the applied displacement from the displacement means,
data processing means for computing the viscoelastic properties of the sample from the measured input and output data associated with the loading member.

According to yet another aspect of the invention there is provided a viscoelastic measurement device, as set forth in any of the preceding paragraphs, incorporating a viscosity or melt flow index measurement device comprising:
a sample measurement enclosure for the or each independent test, loading means for applying a sample under pressure to the enclosure,
a restriction within the enclosure, monitoring means for determining the pressure within the enclosure upstream of the restriction, an output port in the enclosure downstream of the restriction, temperature control and monitoring means for determining the sample temperature within the enclosure, control means for initiating and repeating a test cycle under various pressure and flow conditions for a given temperature, measuring means for measuring the pressure and flow conditions within the enclosure, data processing means for computing the viscosity or melt flow index from successive measurements of pressure and flow rate through the output orifice or restriction.

According to a still further aspect of the invention there is provided a viscoelastic measurement device, as claimed in any of the preceding claims, incorporating supplementary simulation means for simulating the standard derivation of viscosity for a solid, that is melt flow index from measurement of flow rate at a fixed pressure, by effecting a plurality of pressure drop measurements across an orifice through which various rates of flow are delivered, in particular by applying pressure, through a ram extrusion process, and controlled temperature conditions to provide a polymer melt flow, generating and expressing, in digital terms, an algorithm representing the predicted theoretical relationship between pressure and flow and manipulating derived measurement data in logarithmic form to compute, generate and plot graphically the relationship between flow rate and pressure and therefrom to form a notional intercept with a computer-generated reference line of constant pressure related to the standard viscosity measurement test condition profile and deriving the viscosity from that intercept, by a technique of successive approximations involving comparisons between the local values of the constant reference pressure line and the plot of measured pressure and flow rate for a range of flow rates and repeating the comparison until equality is achieved.

There now follows a description of some particular embodiments of a rheometric measurement apparatus (incorporating both viscoelastic and melt flow index measurement, of which only viscoelasticity is of principal concern here, melt flow index being the subject of our copending UK patent application no. 872310 according to the invention, by way of example only, with reference to the accompanying diagrammatic and schematic drawings, in which.

Figure 1:
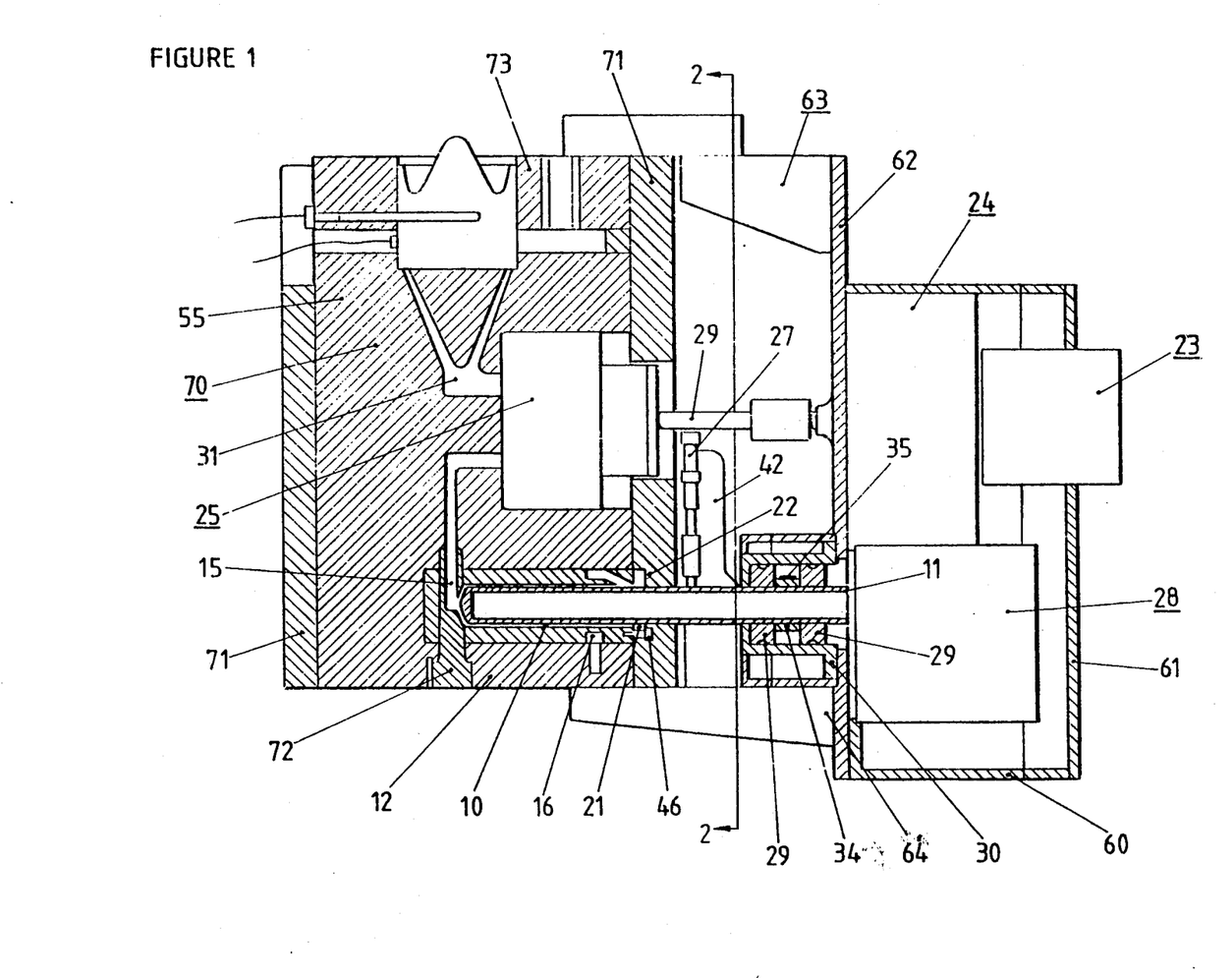
FIG. 1 shows a longitudinal sectional view of the main measurement operating chamber and ancillaries of a viscoelastic measurement apparatus.

Referring to the drawings, and in particular FIG. 1, a viscoelastic measurement chamber 10 is defined by an elongate longitudinal bore in a measurement block 12.

Within the measurement chamber 10 is located a displacement member in the form of a hollow shaft 11 of generally uniform cross-section corresponding to that of the chamber 10, but marginally less in size, in order to leave a carefully predetermined marginal peripheral sleeve-shaped chamber region, into which is supplied a viscoelastic material, for example a polymer melt, under test.

Figure 2:
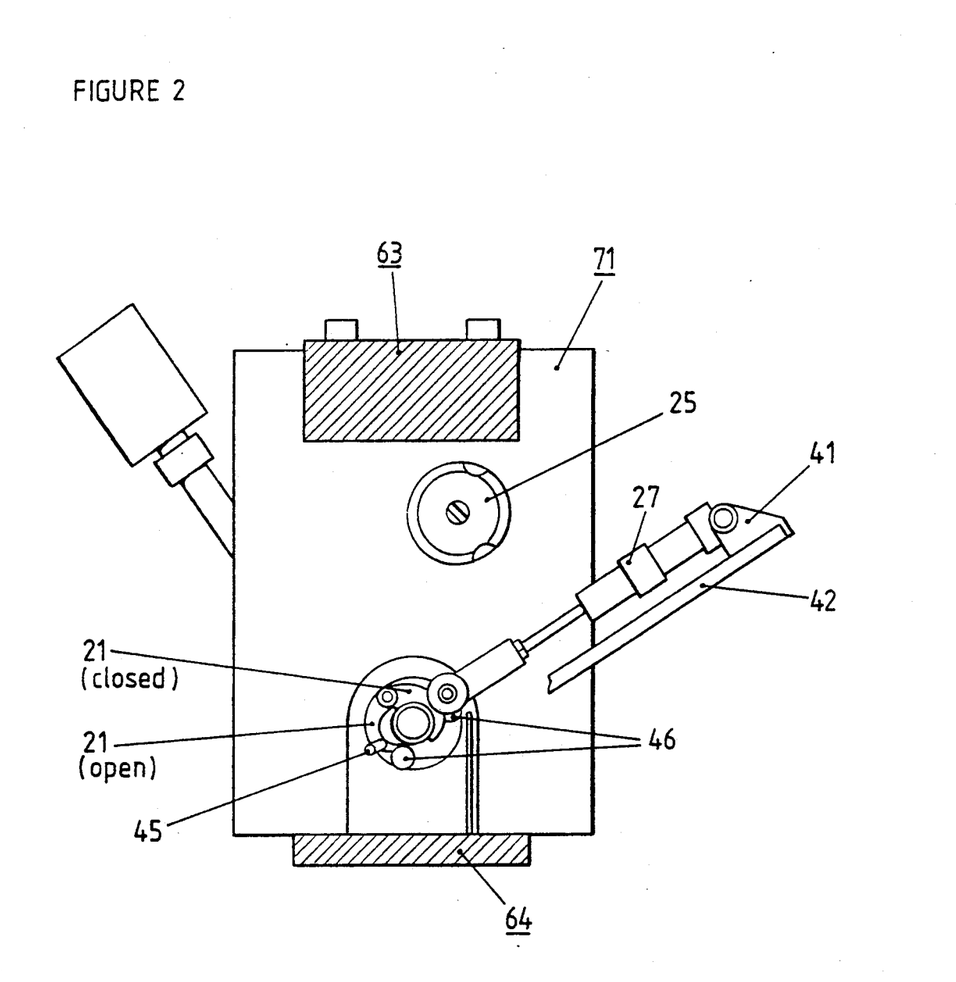
FIG. 2 shows an end sectional view of the apparatus of FIG. 1, taken generally along the line 2—2'.

The chamber 10 is sealingly closable at one end by a shutter door arrangement, shown more clearly in FIG. 2, and comprising a pair of curved profile door segments (21), whose inner profiles combine to wrap around the mouth of the sleeve-shaped chamber, when those door segments 21 are drawn together in the 'closed' condition.

Operation of the doors 21 is through an air cylinder ram 27, whose upper cylinder end is mounted upon a trunnion 41, in turn carried by a cylinder support bracket 42. The doors 21 are mounted on respective pivots 22, about which they are movable, under the constraint of guides 46 (which restrain axial movement), between their open, or prised-apart, condition and their closed together or sealing condition, under the action of the ram actuator 27, the limits of such movement being constrained by door closure rods 45. FIG. 2 illustrates one door 21 in the open condition and another door 21 in a closed position.

The doors 21 allow charging o the test chamber 10 without 'loosing' the input test melt from the outer end of the chamber 10, but in order to equate to the prescribed laboratory standard test, the actual test is performed with the doors open, thus allowing the requisite unfettered deformation of material under test within the chamber. Any excess discharge is 'bled' away through an outlet 16. Similarly, upon changing the chamber 10 contents, a fresh 'charge' is simply urged into the chamber 10 (by a gear pump 25 described later) and, with the doors 21 closed, displaces the previous sample out of the chamber through the outlet 16.

Periodic ingestion of sample material into the chamber 10 is under pressure flow initiated by occasional operation of a gear pump 25 mounted above the chamber block and driven by a stepper motor 23 through a reduction gearbox 24. In this way incremental feeds can be performed and the material is deliver to the chamber 10 in a satisfactory 'unstressed' condition, and without having been forced around any 'sharp' bends or other abrupt path changer (which could be 'remembered' by the material and would distort the test figures) via an inlet passage 15.

In this particular embodiment, in order to facilitate use in conjunction with an (unshown) ram-feeder of test material, typically loaded with a granular ingredient, not otherwise melted, the supply to the gear pump 25 is through a heated pressure or pressurised melter chamber arrangement 55.

The melter 55 is not described herein in detail as it is primarily, albeit not exclusively, concerned with supplementary melt flow index measurement, the subject of our pending UK patent application no. 8723101. Suffice to say that sample material, for example polymer melt, is introduced under controlled pressure, temperature and flow conditions into a feed passage 31 for the gear pump 25.

For other material supply arrangements, for example an extruder discharging pre-melted material, typically from an initial powder ingredient, the pre-melter 55 may be omitted and the test apparatus coupled directly to the extruder output—as described later with reference to the FIG. 4 embodiment.

In order to maintain the temperature stability of the apparatus during measurement operations, the entire material supply, feed and test sections are mounted in a temperature-controlled, 'homogeneous environment' defined within a steel block 70, with an ancillary peripheral 'cuff' heater 71.

To further assist this temperature maintenance, the gear pump 25 incorporates an integral throughput thermometer (not shown).

It should be appreciated that the gear pump 25 effectively acts as a heat exchanger between melted material flowing therethrough and the 'environment' defined by the block 70, 'delicately' balancing the heat inflow and outflows. Internally, the gear pump 25 presents a very large heat exchange surface area, compensating for the otherwise low rate of heat transfer with the test medium.

By this means precise temperature control, for example, to within plus or minus 3 degrees C., is possible, despite the dynamic flow conditions. Thus one sample after another can be loaded, tested and discharged without wasted time for temperature stabilization or equalization. The internal flow paths are suitably short for this.

The feed duct and inlet port 15 to the chamber 10 are formed in a plug 72 received within a complementary recess in the block 70.

The measurement block 12 is a precision-machined component, located within a lateral recess in the walls of the block 70 and sealed therein around its outlet port 16 by sets of axially-spaced peripheral sealing rings 46.

Structurally, the block 70 is supported cantilever-fashion by an upper bracket 63 and a lower bracket 64 of a mounting frame 62, which supports on its opposite side the gearbox 24, stepper motor 23 and 'visco' or displacement drive motor 28, all of which are encased in a cover 60, with an end access lid 61.

At the top of the block 70 is a mounting plate 73 surrounding a controlled melting chamber, of particular relevance to the melt flow index measurement, and for receiving an upright pressurising ram arrangement (not shown).

The plug 72 has a morse taper so that it is a wedge fit in position and passes through a complementary-shaped transverse tapered bore in the measurement block 12. The pre-formed passageway in the end of the plug 72 is thus aligned with the inlet 15 to the measurement chamber 10 and the output flow passage in the block 70 from the gear pump 25.

Reverting to the viscoelasticity measurement components, the shaft 11 is mounted at its outer end, that is outside the chamber 10, in a pair of axially-spaced air bearings 29, enshrouded within a bearing support 30 and casing 35. An air deflector is mounted on the shaft 11 to minimise air escape from the bearing and to obviate a cooling air stream from locally impacting the end of the chamber 10 and disturbing the desired uniform temperature conditions established throughout the block 70.

Figure 3:
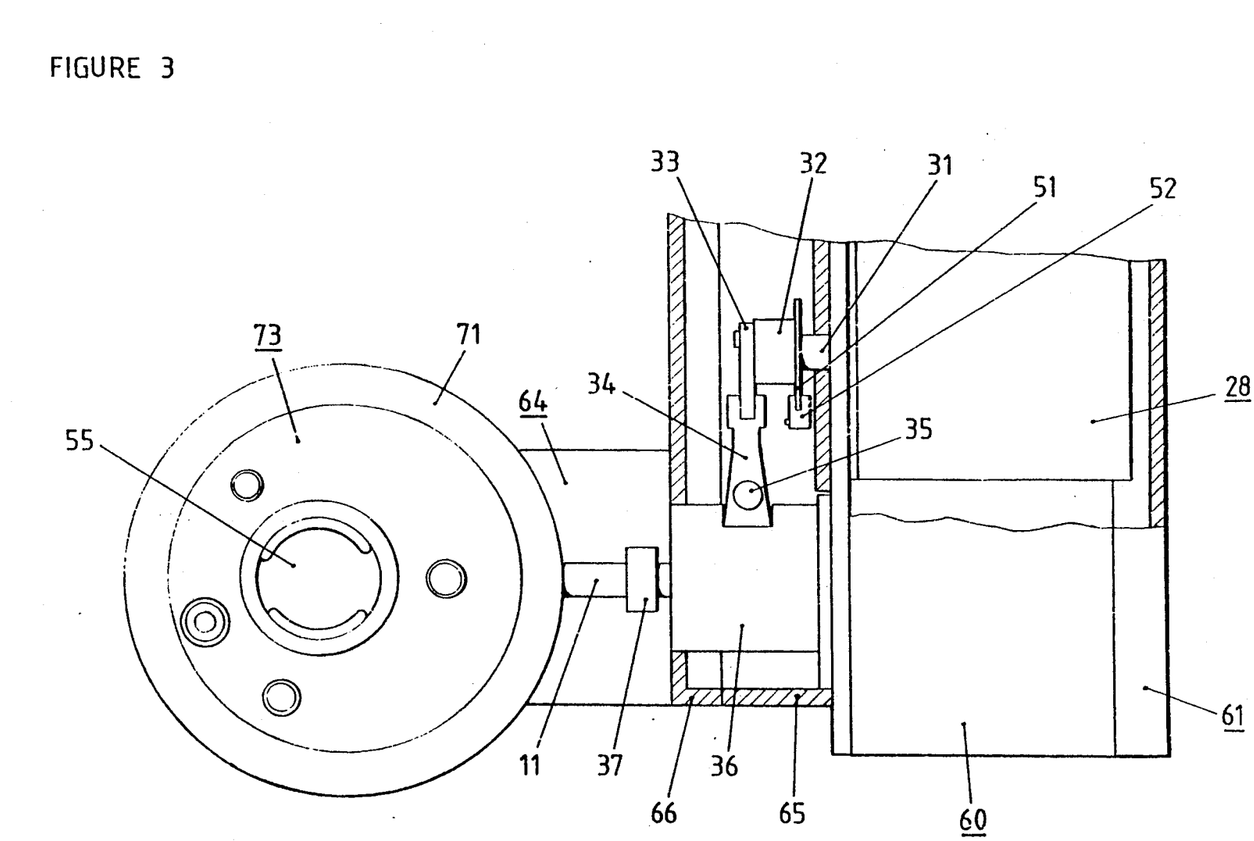
FIG. 3 is a staggered plan view (i.e. from above but at different levels across the section) of the apparatus shown in FIGS. 1 and 2.
Figure 5:
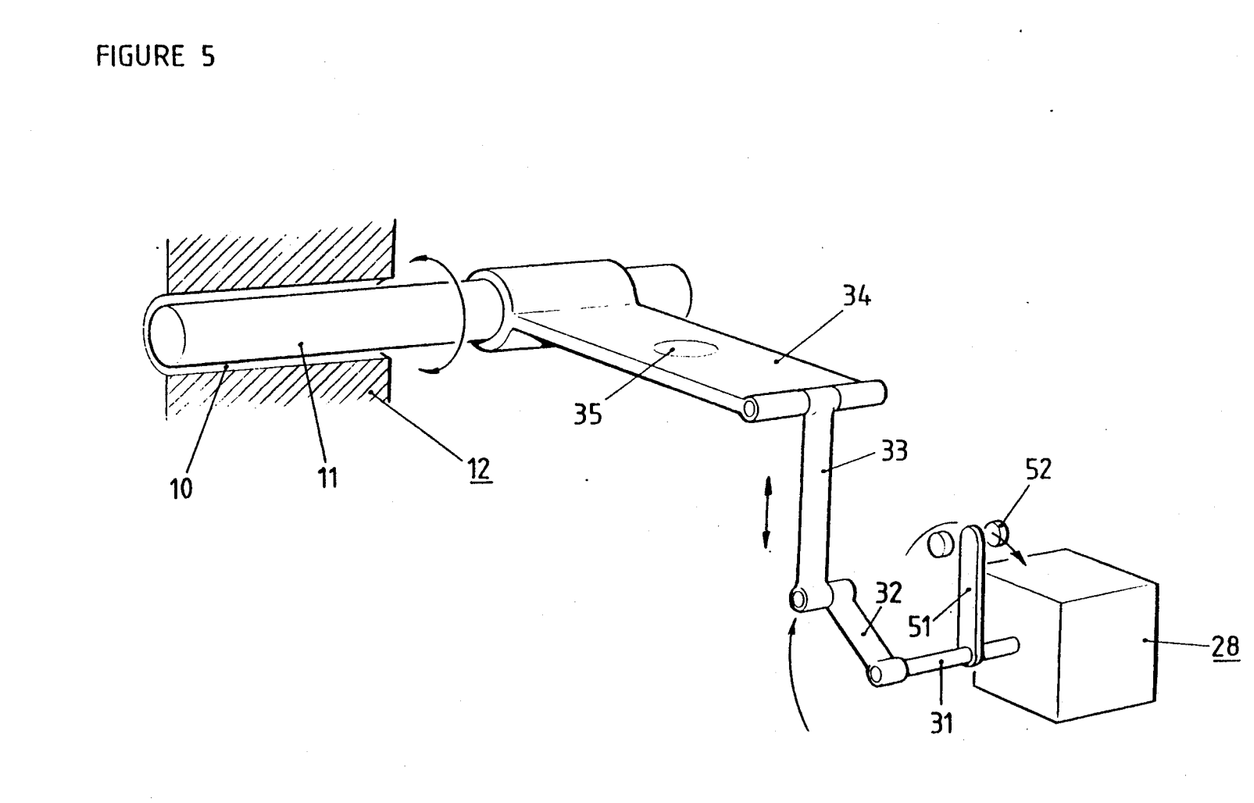
FIG. 5 shows a diagram of the displacement linkage for the apparatus shown in FIGS. 1 to 3.

The shaft 11 is coupled to an oscillatory vibratory mechanism, shown more clearly in FIGS. 3 and 5. Specifically, a transverse or radial torque arm 34 enshrouds the shaft at one end thereof and is coupled to a connecting rod 33, itself fitted to an eccentric 32 mounted on the output shaft 31 of the visco drive motor 28.

FIG. 5 shows diagrammatically the displacement linkage of the shaft 11, which translates an eccentric movement of a radially-displaced pivot on the displacement drive motor output shaft to a cylindrical path about an axis itself moving through a circular path—that is a form of composite eccentric cylindrical path.

A rotational speed and 'angular position' sensor arrangement, is provided for the 'visco' motor 28 and comprises a disc 51 mounted on the shaft 31 and passing between a mutually-aligned light source and sensor 52. Markings on the disc affect the 'optical coupling' between the source and sensor 52, which are connected to circuitry described later, thereby monitoring the shaft 31 movement and angular position.

A strain gauge 35 is mounted on the torque arm 34 and registers both the input displacement to the shaft 11 from the oscillatory vibratory displacement drive previously described and the output or reactionary strain displacement imposed upon the shaft 11 by virtue of its 'local presence' in the chamber 11. The latter, when filled with material under test, resists the deformatory input oscillatory rotational stress applied to the outer end of the shaft 11.

The displacement linkage and drive arrangement described is housed within a casing 65, with an access cover 66.

As shown in FIG. 5, the path of displacement movement of the shaft 11 is the 'product' or net result of the input oscillatory vibrational rotary displacement and the axial and radial restraint of the air bearing 29 in the bearing support 30.

The outer end of the shaft 11 thus undergoes a rotary oscillatory movement and the marginal peripheral chamber defined between its opposite 'inner' end and the walls of the chamber 10 in the measurement block 12 is essentially circular, but eccentric to the chamber axis.

Thus the material under test in the chamber 10 is cyclically loaded and unloaded in a torsional manner, i.e. it is torsionally constrained or deformed (rather than simply crushed) and allowed to relax.

It is the inherent material resistance to deformation and the reassertiveness or speed of reversion to the original undeformed state (i.e. no permanent deformation or purely elastic rather than 'remembered' stress) that characterise the viscoelastic properties—which are crucial to an understanding of how that material will behave when subsequently 'worked' into a desired shape.

Figure 7:
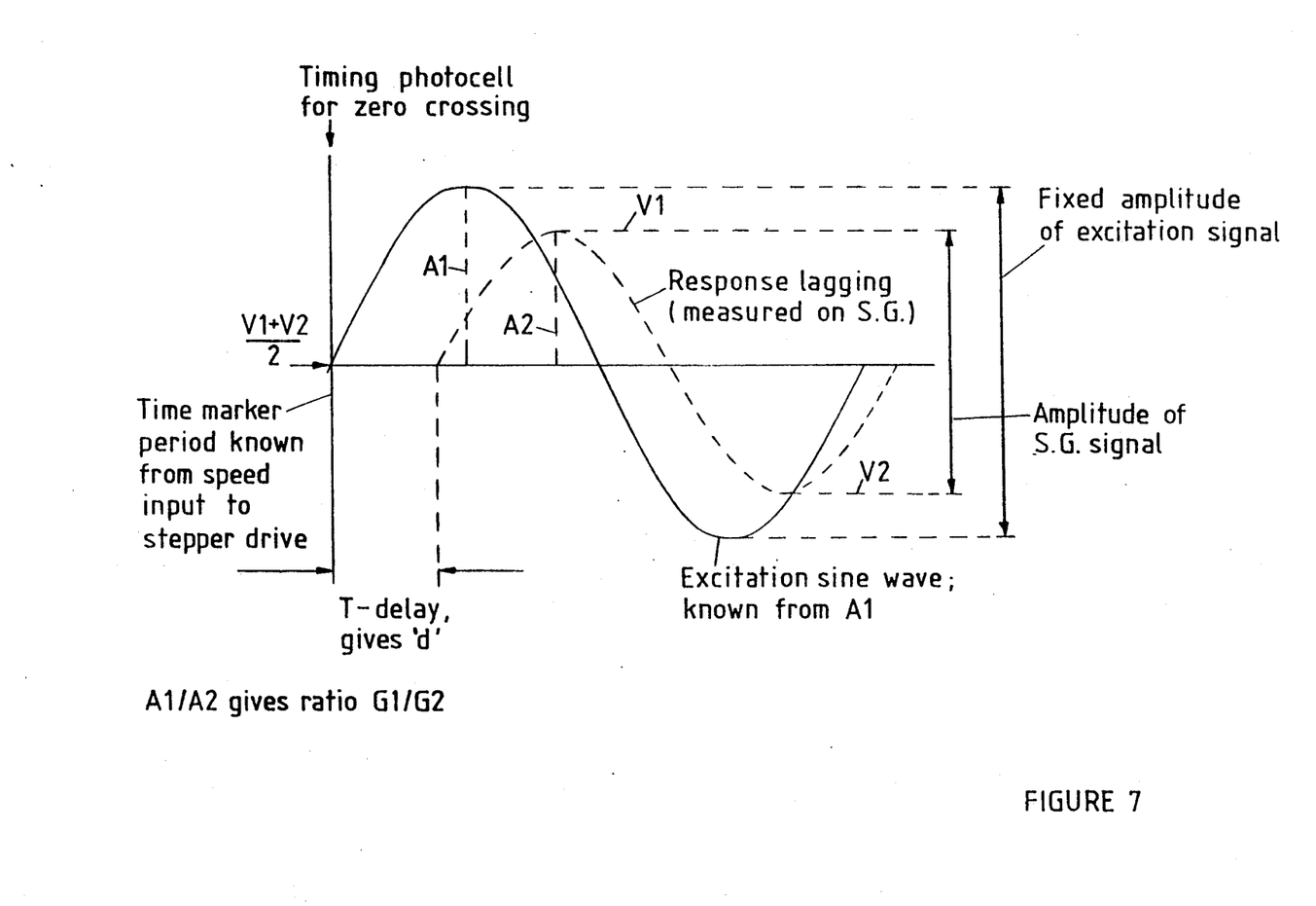
FIG. 7 shows graphically a plot of input and output displacement arising from the linkage shown in FIG. 5.

FIG. 7 shows graphically plot of cyclical (i.e. sinusoidal) input and output or reaction displacement.

The output clearly and necessarily lags behind the input because the material 'presence' (i.e. the material cannot be simply squeezed without offering resistance out of the test chamber, even with the doors opened) and this 'phase' difference in turn forms the basis of measurement of viscoelasticity, when taken in conjunction with the monitoring of the input shaft rotation and the attendant generation of time marker points.

The relative amplitudes $A_1/A_2$ of input and output displacement waveforms give mathematically the ratios $G_1/G_2$ of the strain rate factors; whereas the phase lag between input and output gives the shear strain factor.

It should be appreciated that viscoelastic measurement can be undertaken according to the invention upon ongoing sample batches during production and any deviations from the 'norm' of required characteristics for the desired end-manufacturing use corrected and re-checked. Such ongoing monitoring to high standards of accuracy enables the machine to be used in plastics production and in component production from plastics ingredient.

The sequence of measurement operations is as follows:

A sample from a batch of material under test is driven through the gear pump 25 into the measurement chamber 10, with the doors 21 securely closed, except perhaps initially to allow exhaust of residual atmosphere.

Once a predetermined volume loading has been achieved of the chamber 10, by a predetermined running period of the gear pump 25, the feed is halted by stopping the gear pump 25, whereupon the doors 21 are opened. The stepper motor drive 23 facilitates this by allowing incremental loading of successive repeated 'shots' of ingredient under test, each of predetermined volume or quantity form the gear pump internal dimensions and the rate of incremental rotation. Moreover, the stepper motor 23 lends itself to controlled digital drive by electrical pulses from the control circuitry described later.

With the chamber 10 filled and loading halted, any excess material can bleed out of the outlet passage 16. The 'visco' drive motor 28 is then triggered and the end of the shaft 11 eccentrically displaced as previously described. This displacement is translated along the length of the shaft 11 to the other inner end located within the chamber 10 and the material loaded therein is subjected to cyclically torsional applied stress. This continues for a predetermined time period sufficient for the conditions to stabilise and successive measurements taken to provide a cumulative picture of the sample characteristics, from repeated electronic circuitry computations and approximations, again as described later.

Figure 4:
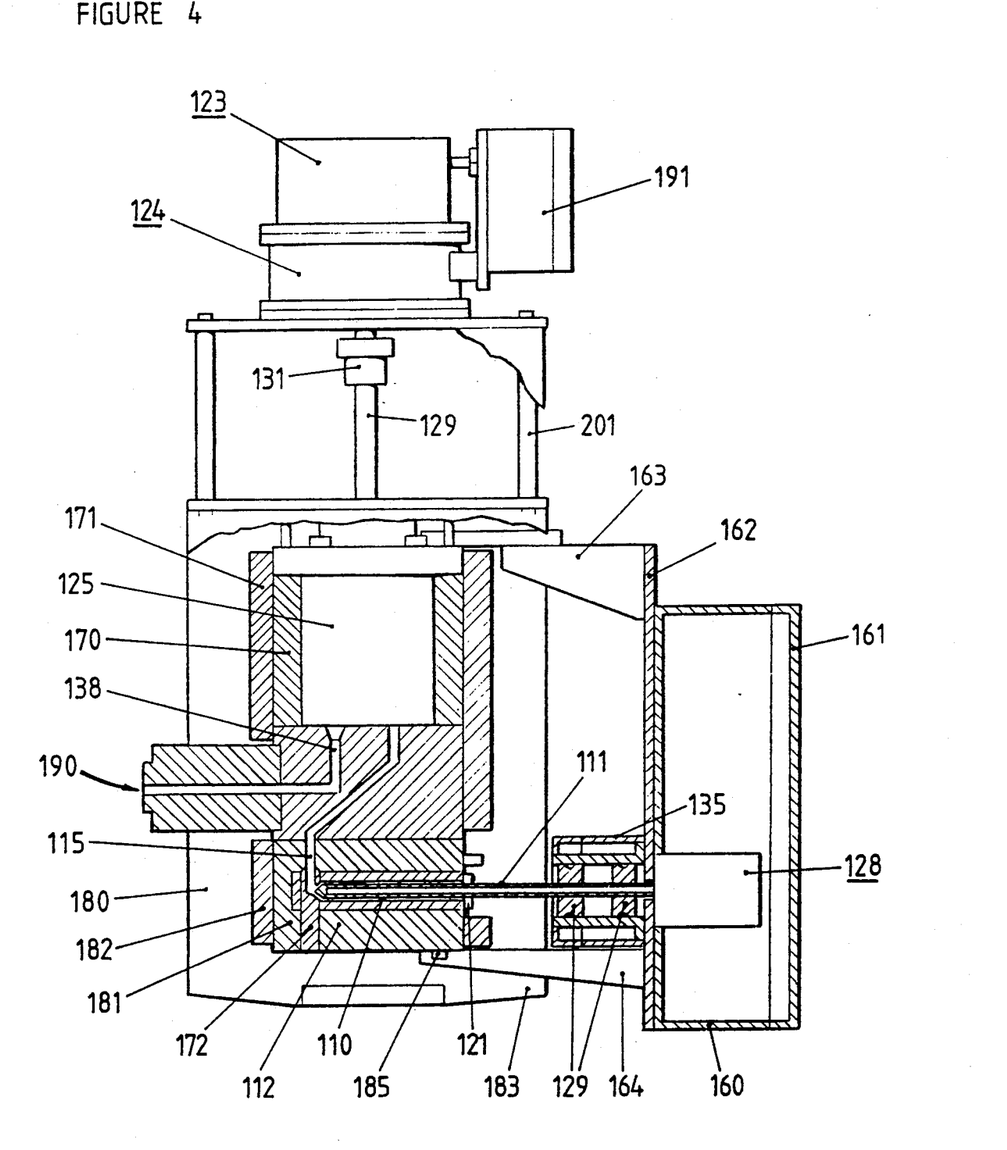
FIG. 4 shows an alternative compact apparatus arrangement to that shown in FIGS. 1 to 3.

Referring to FIG. 4, a compact measurement arrangement, is particularly, but not exclusively, concerned with direct fitment to an extruder (e.g. a screw or auger extruder, working with a powder ingredient, and although not illustrated, would be disposed to the left as viewed in FIG. 4), which supplied a pre-molten stream, e.g. of a polymer melt, 190, which is fed through an inlet passage 138 direct to a gear pump 125, 'buried' in an upper mounting block 170.

An outlet passage 136 feeds material from the gear pump 125 through the upper block 170 to a test chamber 110 in a chamber block 112 'buried' in a lower mounting block 181.

The upper and lower blocks 170 and 181 are surrounded by respective upper and lower 'cuff' or peripheral collar heaters 171 and 182, controlled by thermometers (not shown), and which thereby maintain a homogeneous temperature-controlled environment for the measurement test within the chamber 110.

The gear pump 125 is driven through a drive shaft 129, coupling 129 and gearbox 124, by a stepper motor 123, with encased electrical control gear 191. The (upper) gear motor drive is separated from (low) the measurement assembly by spacer rods 201, with an optional protective guard casing (not shown), in turn mounted by bolts on the upper surface of the upper block 170 and thus does not impair the temperature control by acting as a local distorting heat sink.

The measurement assembly is supported by upper and lower brackets 163, 164 respectively upon a support plate 162, on the opposite side of which is mounted a displacement drive motor 128, coupled to a displacement shaft 111, inserted at one end (remote from the drive 128) into the measurement chamber 110 and supported at its other 'outer' end (adjacent the drive 128) by an air bearing assembly 129.

An outer casing 160, with an access cover 161 enshrouds the drive 128 and a casing 135 covers the air bearing 129. A further cover 180 encloses the measurement assembly and incorporates an drain hole 183 for any leaks from the chamber 110, which is fitted at its outer ends with door seals 121 on pivots 122 for embracing the shaft 111.

A main drain outlet 185 from the chamber 110 allows sample changes.

The chamber block 112 is located within the lower mounting block 181 by a tapered pin 172 incorporating the inlet passage 115 to the chamber 110.

Operation of the test is as with the apparatus described with reference to FIGS. 1 to 3, but in addition to physical compactness in terms of overall layout, with short and 'progressively-contoured' internal flow paths, the FIG. 4 arrangement facilitates the precise temperature control required for precision test measurements. Thus varying input temperatures (from the extruder) are rapidly offset and do not disrupt the test.

Although not reliant upon the following theoretical basis, which is advanced rather by way of background information, the present invention takes advantage of the measurement of viscoelasticity by making a sample of known quantity and constraining it within a chamber of known dimensions (i.e. inner and outer radii and length) in order to define the 'visco' defining viscoelasticity) the known mathematical expression for defining viscoelasticity) in relation to the sample generated.

The constraining chamber is relatively long (in relation to its cross-section), and is equivalent or approximates to conditions in which shear strain in a coni-cylindrical sample confine equals the ratio of the angular displacement of the sample to the angle between the inner cone displacement plate surface and outer chamber wall. The applied stress is thus proportional to (shear) strain and (shear) strain rate; linearly (i.e. stress/strain=constant) for small strains and non-linearly for large strains.

With the various apparatus described, an alternative door seal arrangement may be used. For example, the displacement shaft itself may be shaped in places to afford a local sealing action with respect to the chamber walls—thus a coni-cylindircal chamber (i.e. a cylindrical body with conical, tapered or wasted section ends) with a complementary-shaped 'bob' shaft would allow selective local sealing of the chamber by axial displacement of the shaft to engage the conic sections.

Alternatively, an annular bellows of elastomeric material (i.e. on which would automatically relax and return to its un-displaced shape) could be fitted around the mouth of the measurement chamber, with provision for selective inflation, for example by air pressure delivered through a hollow displacement shaft section.

Another significant feature of all the apparatus shown is the possibility of, or facility for, integrating measurement of viscoelasticity with melt flow index (MFI). by using common premelting and/or pressure pumping stages in addition to the controlled-temperature environment.

Thus the output of the gear pump may be divided into two paths, one to a viscoelastic measurement chamber and the other to an MFI measurement chamber, both chambers being located in one and the same mounting block. So, for example, the MFI measurement the subject of our co-pending UK patent application no. 8723101 may be integrated with the viscoelastic measurement of the present invention to constitute another aspect thereof.

In practice the MFI test, which essentially requires a continuous flow under known pressure and temperature conditions, would be carried out with the gear pump operating—and at the same time loading the viscoelastic chamber and purging its previous contents by positive displacement with the fresh sample. The gear pump would be halted after the MFI test cycle (of, say, 10 minutes) and the viscoelastic test performed, with the chamber doors opened, by triggering the displacement drive motor.

Figure 6:
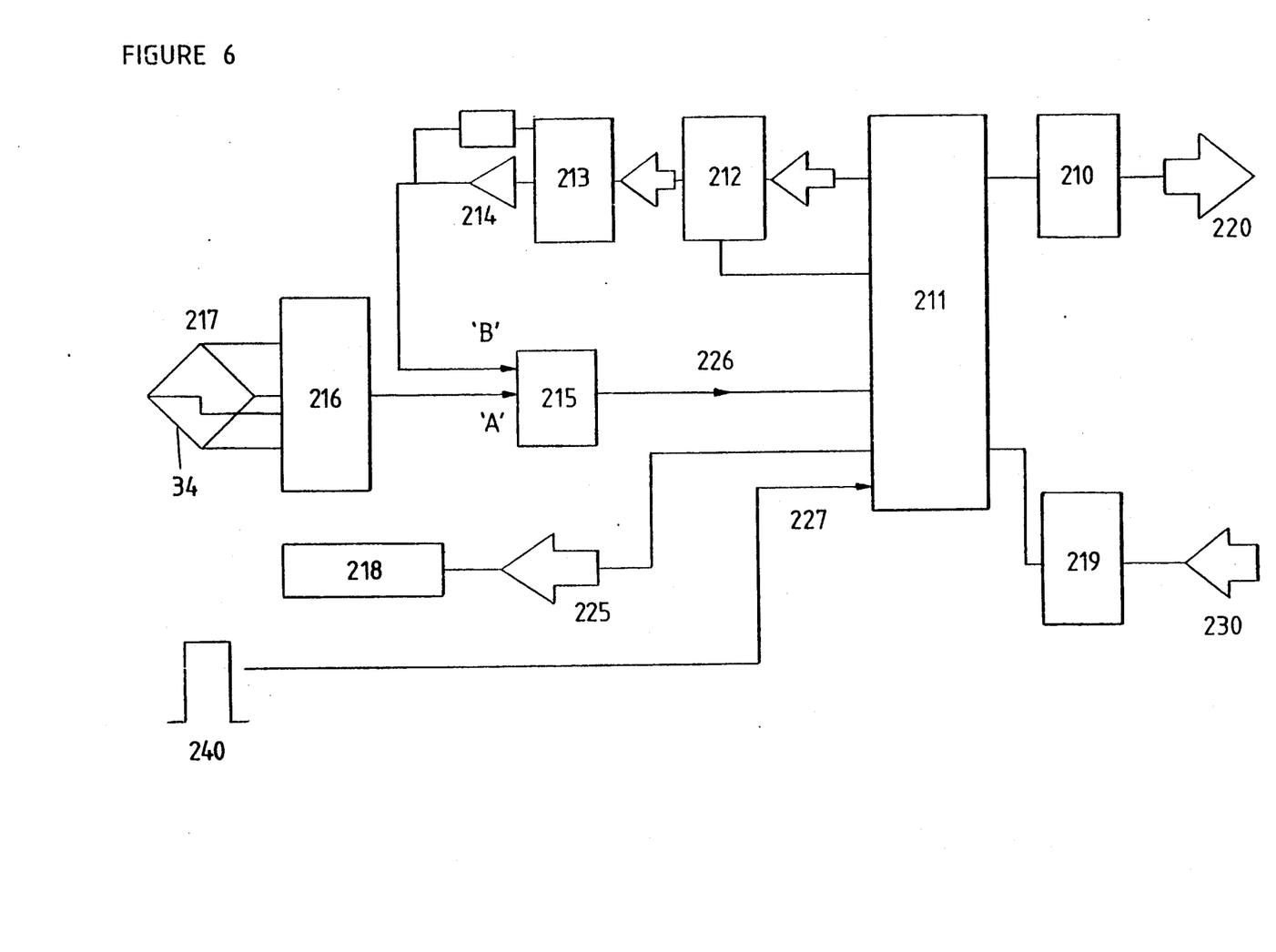
FIG. 6 shows a computerised electronic circuit for effecting the measurement in the apparatus of FIGS. 1 to 5.

The computations involved in the test are performed by a computerised circuit arrangement, shown in block schematic form in FIG. 6. Thus the strain gauge 35 is represented electrically by a bridge circuit 217 across whose arms is connected a differential amplifier 216, whose output is fed to comparator 215, to other input of which is connected a variable reference signal generated by a dedicated microprocessor 211. The latter, through a latch 212 and digital to analogue converter (DAC) 213 applies varying voltages to the comparator 215 to affect the comparison with the monitored strain gauge voltage and in turn switch the comparator output 226 from positive to negative—i.e. a 'polarity crossing-'—which is in turn registered by the microprocessor 211.

Timing pulses 227 from the optical sensor arrangement 51, 52 on the displacement drive motor output shaft 31 provide a reference for the 'start' position of a test cycle, the rate of rotation and time of rotation being controlled by the microprocessor.

A variable gain control 218 controlled by a gain-setting signal 225 from the processor 211 effectively scales the sensitivity of measurement, as described later.

Similarly, a frequency setting unit 219 is able to receive commands 230 (relating to the measurement waveform frequency—in turn related to the rotational speed of the displacement drive) from a host computer (not shown—but which may be an adapted proprietary industrial control unit) which receives a gain setting, time delay and torque amplitude signal 220 from a setting unit 210 linked to the processor 211.

In more detail, the sequence of operations, as depicted in FIGS. 7, 8, 9 and 10, is that a signal is sent from the differential amplifier 216 and applied as an input 'A' to the comparator 215, whose other input 'B' is derived from the DAC 213, and which furnishes a '0' output if A>B or a '1' output if B>A.

Thus for a positive input waveform peak, a zero is loaded into the DAC 213 when an optical trigger 51/52 pulse signal is received. The comparator 215 thereby acquires the time for the zero crossing.

The computer then waits for the strain gauge signal to exceed the comparator signal, whereupon it 'increments' the DAC output by a predetermined value.

This increment and subsequent test procedure is repeated until the increment no longer produces a test to shown that the DAC 213 output is less than the strain gauge derived output value. This is the positive peak value.

Similarly, the negative peak is found by covering the DAC 213 from zero.

Figure 8:
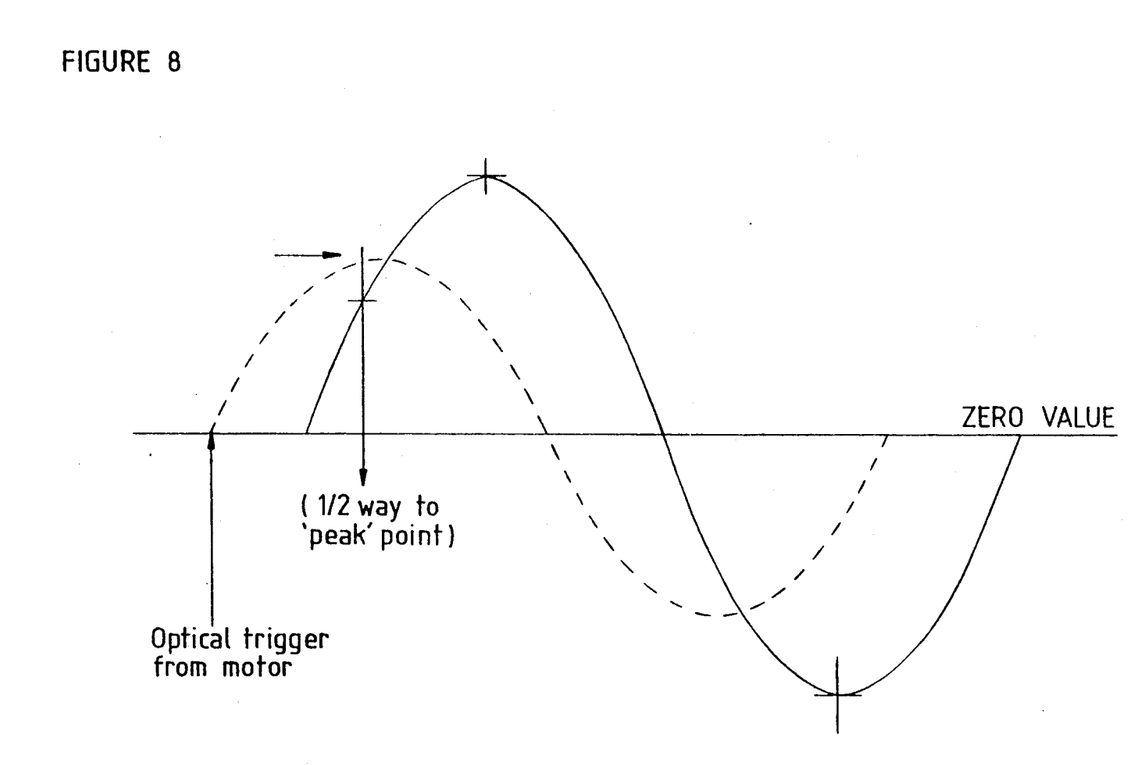
FIG. 8 shows an elaboration of the FIG. 7 waveforms for low frequency measurement.

With low frequencies the DAC 213 will thus effectively 'track' the SG waveform.

As depicted in FIG. 8, at a point marked ½ way to the peak point (which can be recognised from the known period or drive frequency/rate of the stepper motor driving the 'visco' displacement arm) the value of the DAC is noted. If the signal can be amplified, then the switched gain (SG) of the SG amplifier 218 is changed (by control signal 225), such that the final predicted value of the peak lies between ½ and full-scale of the DAC 213. The gain can be switched in multiples of 2 by the computer.

Figure 9:
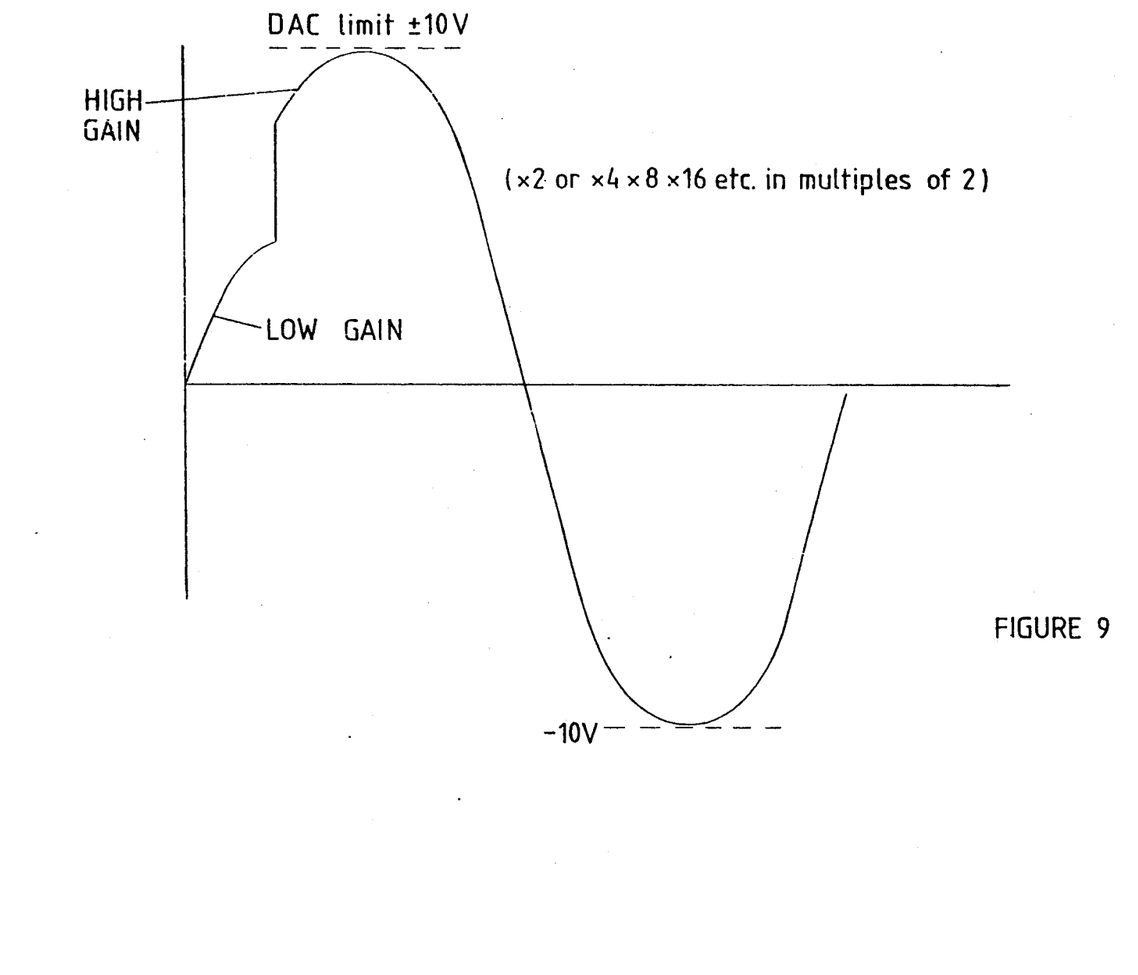
FIG. 9 shows a variation of the waveforms of FIGS. 7 and 8 for high frequency measurement.

At higher frequencies, as the frequency increases, the foregoing 'track' method is no longer fast enough to keep pace with the rapidly-changing amplitude of the SG waveform.

Nevertheless, it si important to use the track method at low frequencies because the time taken for the test would otherwise be very long if all the data were not taken within a single cycle.

At high frequencies a different strategy is used, as depicted in FIG. 9. Specifically, the DAC 213 is loaded first with zero and the zero crossing time is noted. Then the DAC 213 is loaded with ½ its positive full scale potential value. If the positive SG peak is below this value, then the DAC 213 is raised to $\frac{1}{2}+\frac{1}{4}$ positive full scale. If the positive peak is still below this value then the gain is raised until the DAC 213 ½ scale is exceeded for the first time. Then the DAC 213 is raised to $\frac{1}{2}+\frac{1}{4}$ positive full scale and a retest is made.

If the value is $>\frac{1}{2}+\frac{1}{4}$, then the DAC 213 is raised to $\frac{1}{2}+\frac{1}{4}+\frac{1}{8}$.

If the value is $<\frac{1}{2}+\frac{1}{4}$, then the DAC 213 is reduced to $\frac{1}{2}=\frac{1}{8}$ ... and so on until the positive peak is established in successive approximations.

Figure 10:
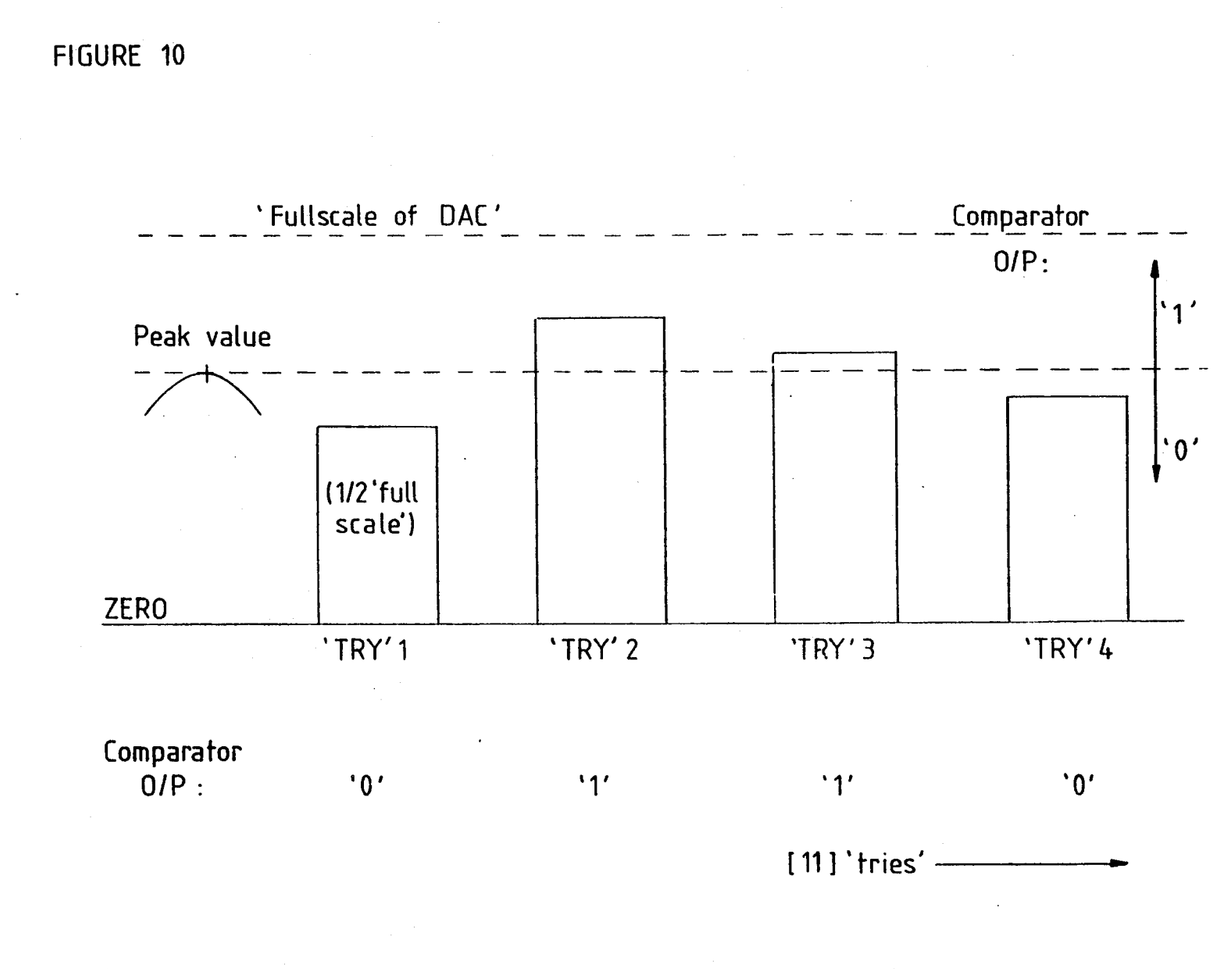
FIG. 10 shows a multiple pulse stream effecting a successive approximation technique for measuring the waveforms of FIGS. 7, 8 and 9.

The maximum number of cycles=11, with 8 gain switches=19.

Similarly, the negative peak is found with the maximum number of cycles at 11, because the same gain is used with the negative cycle.

The zero value of the SG is being continually updated in the light of experience of the positive an negative peaks; zero means ½ way between the positive and negative peaks. The changeover to successive approximations is about 30 c.p.s.

I claim:

1. A viscoelastic measurement device comprising a measurement chamber (10) to receive a sample whose viscoelasticity is to be measured, a displacement member (11) located in said chamber, displacement means (34) for displacing the displacement member within the measurement chamber in such a way as to apply a rotary oscillatory deformatory stress to a sample located therein, measurement transducer means (35) for detecting the input deformatory displacement, measurement transducer means (35) for detecting the output or reaction deformatory movement or action of the sample, calculator means (211) for calculating the viscoelasticity from the input and output data.

2. A rheometric measurement device for affording data upon the rheological properties and thus the processability of a sample. in particular a polymer melt, including the measurement of elasticity under applied stress, in particular a rotational or torsional movement, that is by rotational rheology or rheometrics, and optionally the measurement of viscosity or melt flow index, the device comprising:

a sample chamber to receive a sample under test,
loading means for loading a sample into the chamber,
seal means for restraining the sample within the chamber,
pressurising means for pressurising the sample within the chamber or upon its entry thereinto,
pressure relief means for allowing the controlled egress of material from the chamber,
temperature control means for maintaining the sample at a predetermined temperature,
loading means for applying a cyclically repeated controlled loading force to the sample,
detector means for detecting the reaction of the sample to the applied loading,
computer means for computing from the reaction data the rheometric properties of the sample.

3. A viscoelastometer for measuring the viscoelastic properties of a sample under varying applied stress and monitored strain reaction conditions and comprising:

a constant temperature enclosure,
means for loading or applying a constant temperature flow of sample material, or a polymer street, to the enclosure,
means for restraining the sample within the enclosure,
controlled exit means for allowing a controlled output of sample material from the enclosure,
a rotary loading member located within the enclosure and defining a marginal space therebetween and the enclosure walls,
controlled displacement means for cyclically moving the loading member within the enclosure with a rotary oscillatory motion,
sensor means for monitoring the displacement of the loading member and the reaction forces thereupon from the sample material within the enclosure to the applied displacement from the displacement means,
data processing means for computing the viscoelastic properties of the sample from the measured input and output data associated with the loading member.

4. A viscoelastic measurement device, as claimed in claim 1, wherein the chamber is cylindrical and the displacement member comprises a cylindrical shaft which is closely interfits therewith, leaving a marginal peripheral space therebetween for said sample.

5. A viscoelastic measurement device as claimed in claim 1, wherein said displacement means comprises a rotary oscillatory drive from a prime mover located externally of the chamber, whereby the sample therein is subjected to cyclically varying torsional excitation stress.

6. A viscoelastic measurement device, as claimed in claim 1, incorporating movable seals externally of the chamber about the displacement member, and selectively operable in order to inhibit egress of sample material from the chamber during filling of the chamber, but releasable during subsequent testing.

7. A viscoelastic measurement device, as claimed in claim 1, wherein the chamber incorporates an annular passageway adjacent a sealed chamber end where the displacement member emerges, and communicating with a drain hole to allow flushing through of the chamber contents, with minimal escape.

8. A viscoelastic measurement device, as claimed claim 1, wherein the displacement member comprises a shaft mounted in a low friction bearing support, which is arranged to provide axial and radial constraint of the shaft.

9. A viscoelastic measurement device, as claimed in claim 8, wherein a supplementary torque arm is connected to the shaft at the centre of the bearing assembly and is in turn linked to a connecting rod mounted upon an eccentric fitted to the output drive shaft of a variable speed motor.

10. A viscoelastic measurement device, as claimed in claim 9, wherein the motor causes the shaft to perform rotary oscillations in a near sinusoidal manner, through a small constant angle appropriate to the derivation of the viscoelastic properties of the sample.

11. A viscoelastic measurement device, as claimed in claim 10, incorporating a strain gauge on the torque arm to monitor the torque forces applied to the shaft in both amplitude and time.

12. A viscoelastic measurement device, as claimed in claim 11, wherein the motor drive shaft has a slotted disc mounted thereupon, with a mutually-aligned photo diode sensor and light source arranged to register the rotation of the disc by the slot movement, in order to provide reference timing pulses when the displacement shaft is at the mid-points of its cycle of oscillation.

13. A viscoelastic measurement device, as claimed in claim 12, wherein the drive motor speed is selectively adjustable to monitor the viscoelastic properties at various angular frequencies of shaft displacement.

14. A viscoelastic measurement device, as claimed in claim 13, wherein a microprocessor is employed to compute the desired viscoelastic properties parameters, using the inputs of the drive motor speed or angular position and strain gauge torque measurement.

15. A viscoelastic measurement device, as claimed in claim 14, wherein the microprocessor incorporates a peak detecting circuit using successive digital incremented or decremented approximations to a comparator to which are applied the strain gauge measurements, the process being repeated to cover both positive and negative amplitude peaks.

16. A viscoelastic measurement device, as claimed in claim 15, wherein the microprocessor incorporates a timer for registering the phase difference between the applied excitation of the torque arm and the strain gauge signal, the timer being triggered by the photo diode sensor to start the timing sequence and being stopped by the strain gauge amplitude crossing the zero level between opposite positive and negative amplitude peaks, the peak detector setting a comparator at the mathematical between-peaks mid-point of the applied deformatory stress.

17. A viscoelastic measurement device, as claimed claim 1, incorporating a viscosity or melt flow index measurement device comprising:

a sample measurement enclosure for the or each independent test, loading means for applying a sample under pressure to the enclosure,
a restriction within the enclosure,
monitoring means for determining the pressure within the enclosure upstream of the restriction,
an output port in the enclosure downstream of the restriction, temperature control and monitoring means for determining the sample temperature within the enclosure, control means for initiating and repeating a test cycle under various pressure and flow conditions for a given temperature, measuring means for measuring the pressure and flow conditions within the enclosure, data processing means for computing the viscosity or melt flow index from successive measurements of pressure and flow rate through the output orifice or restriction.

18. A viscoelastic measurement device, as claimed in claim 1, incorporating simulation means for simulating the standard derivation of viscosity from measurement of flow rate at a fixed pressure, by effecting a plurality of pressure drop measurements across an orifice through which various rates of flow are delivered, in particular by applying pressure, through a ram extrusion process, and controlled temperature conditions to provide a polymer melt flow, generating and expressing, in digital terms, an algorithm representing the predicted theoretical relationship between pressure and flow and manipulating derived measurement data in logarithmic form to compute, generate and plot graphically the relationship between flow rate and pressure and therefrom to form a notional intercept with a computer-generated reference line of constant pressure related to the standard viscosity measurement test condition profile and deriving the viscosity from that intercept, by a technique of successive approximations involving comparisons between the local values of the constant reference pressure line and the plot of measured pressure and flow rate for a range of flow rates and repeating the comparison until equality is achieved.

* * * * *